US00PP14430P39

(12) United States Plant Patent
Pieters

(10) Patent No.: US PP14,430 P3
(45) Date of Patent: Dec. 30, 2003

(54) CHRYSANTHEMUM PLANT NAMED 'GEDI TWO PIN'

(50) Latin Name: *Chrysanthemum morifolium*
Varietal Denomination: Gedi Two Pin

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 10/137,794

(22) Filed: May 1, 2002

(65) Prior Publication Data

US 2003/0208823 P1 Nov. 6, 2003

(51) Int. Cl.[7] ..... A01H 5/00
(52) U.S. Cl. ..... Plt./294
(58) Field of Search ..... Plt./294, 286

(56) References Cited

PUBLICATIONS

Brummitt, Horticultural Science Chrysanthemum once again, The Garden, 1997, pp. 662–663.*

* cited by examiner

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar is disclosed, characterized by a spoon-tip daisy-type inflorescence, consistent flowering response to short days, blooming consistently after 49 days of short day length, free branching habit, white ray florets, a very uniform round growth habit, and a large quantity of blooms per flowering branch.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Gedi Two Pin.'

BACKGROUND OF THE INVENTION

The new cultivar is a product of hybridization of a female parent variety, 'Papiro' (U.S. Plant Pat. No. 12,998) and a male parent variety 'Tartino Yellow' (undistributed in the United States). The new cultivar was discovered and selected by the inventor in September 1998.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Gedi Two Pin' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Pin.' These characteristics in combination distinguish 'Gedi Two Pin' as a new and distinct Chrysanthemum cultivar:

1. Spoon-tip daisy-type inflorescence,
2. Consistent flowering response to short days, blooming consistently after 49 days of short day length,
3. Free branching habit, 4. White ray florets,
5. Very uniform round growth habit, and
6. Large quantity of blooms per flowering branch.

Plants of the new cultivar are similar to plants of the female parent variety, 'Papiro' in most horticultural characteristics, however plants of the new cultivar have ray florets of a different shape and more inflorescences per flowering branch. Plants of the new cultivar also have fewer ray florets per inflorescence than plants of the female parent variety.

Plants of the new cultivar are similar to plants of the male parent variety, 'Tartino Yellow,' however the new cultivar has ray florets of a different color than plants of the male parent variety. Plants of the new cultivar are also taller than plants of the male parent variety and have a different type of inflorescence than plants of the 'Tartino Yellow' variety.

In comparison to the commercially available variety 'Rome' (U.S. Plant Pat. No. 13,032), 'Gedi Two Pin' blooms naturally one to two weeks later, has a wider diameter inflorescence, has a different type of inflorescence, and has more blooms per flowering branch.

BRIEF DESCRIPTION OF THE PHOTOGRAPH

The photograph shows a plant of 'Gedi Two Pin' grown in a six-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in Oxnard, Calif. during the month of December and January. The age of the observed plants is 87 days from a rooted cutting. The growing temperature ranged from 50° to 68° F. at night to 60° to 75° F. during the day. Measurements and numerical values represent averages of typical flowering types.

Botanical classification: *Chrysanthemum morifolium* cultivar 'Gedi Two Pin'.
Commercial classification: Garden-type Chrysanthemum.
Parentage: Hybridization of a female parent variety, 'Papiro' (U.S. Plant Pat. No. 12,998), and a male parent variety 'Tartino Yellow' (undistributed in the United States).

PROPAGATION

Time to rooting: 7 to 14 days at approximately 21° C.
Root description: Fine, fibrous.

PLANT

Growth habit: Mounding herbaceous perennial.
Height: Approximately 26.5 cm.
Spread: Approximately 33 cm.
Growth rate: Moderate.
Branching characteristics: Free branching.
Length of lateral branches: Approximately 28 cm.
Number of leaves per lateral branch: Approximately 17.

FOLIAGE

Leaf:
- *Arrangement.*—Alternate.
- *Average length.*—Aproximately 5.2 cm.
- *Average width.*—Approximately 4.9 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near 137A. Young foliage under side: Near 138B. Mature foliage upper side: Near 137A. Mature foliage under side: Near 138B. Venation upper side: Near 142C. Venation under side: Near 138C.
- *Venation type.*—Net.

Petiole:
- *Average length.*—Approximately 2.1 cm.
- *Color.*—Near 137A.
- *Diameter.*—Approximately 0.2 cm.

BLOOM

Inflorescence:
- *Flowering habit.*—Induced by darkness period greater than 13.5 hours, approximately 49 days of appropriate day length required to induce and develop blooms.
- *Inflorescence form.*—Spoon Tip Daisy.
- *Natural flowering season.*—Approximately the middle two weeks of September.
- *Number of inflorescences per lateral branch.*—Approximately 17.
- *Inflorescence diameter.*—Approximately 3.5 cm.
- *Inflorescence depth.*—Approximately 1.2 cm.
- *Inflorescence longevity on plant.*—Approximately 24 days.
- *Persistence.*—Persistent.
- *Disk diameter.*—Approximately 1.1 cm.

Ray florets:
- *Appearance.*—Matte.
- *Texture.*—Smooth.
- *Average number per flower.*—38.
- *Shape.*—Spatulate.
- *Aspect.*—Flat.
- *Margin.*—Two-thirds of base-cylindric, remaining one-third at tip-cymbiform.
- *Apex.*—Retuse.
- *Length.*—Approximately 1.8 cm.
- *Width.*—Two-thirds of base — approximately 0.2 cm, remaining one-third at tip — approximately 0.4 cm.
- *Color.*—Upper surface at first opening: Near 155D. Upper surface at maturity: Near 155D. Upper surface at fading: Near 155D. Under surface at first opening: Near 155D. Under surface at maturity: Near 155D. Under surface at fading: Near 179C.

Disc florets:
- *Appearance.*—Shiny.
- *Texture.*—Smooth.
- *Average number per flower.*—Approximately 151.
- *Shape.*—Cylindric.
- *Apex.*—Obtuse.
- *Average length.*—Approximately 0.4 cm.
- *Average width.*—Approximately 0.1 cm.
- *Color.*—At first opening: Near 2B. At maturity: Near 6A. At fading: Near 7A.

Peduncle:
- *Length.*—At terminal end (shortest): Approximately 3 cm. At lateral end (longest): Approximately 8.5 cm.
- *Angle to stem.*—Acute.
- *Strength.*—Moderate.
- *Color.*—Near144A.
- *Habit.*—Upright.
- *Diameter.*—Approximately 0.1 cm.
- *Surface texture.*—Lightly pubescent.

Inflorescence bud:
- *Length.*—Approximately 0.5 cm.
- *Diameter.*—Approximately 0.6 cm.
- *Form.*—Globular.
- *Color.*—Near 155D.

Involucral bracts (phyllaries):
- *Appearance.*—Matte.
- *Texture.*—Lightly pubescent.
- *Number.*—Approximately 28.
- *Shape.*—Ovate.
- *Margin.*—Entire.
- *Apex.*—Subacute.
- *Length.*—Approximately 0.6 cm.
- *Width.*—Approximately 0.4 cm.
- *Color.*—Upper side: Near 144A. Under side: Near 144A.

REPRODUCTIVE ORGANS

Ray florets:
- *Number of pistils per flower.*—1.
- *Stigma shape.*—2 branched.
- *Stigma color.*—Near 6A.
- *Style color.*—Near 1D.
- *Style length.*—Approximately 0.4 cm.
- *Stamens.*—Absent.

Disc florets:
- *Number of pistils per flower.*—1.
- *Stigma shape.*—Two-branched.
- *Stigma color.*—*Near* 13A.
- *Style length.*—Aproximately 0.2 cm.
- *Style color.*—Near 154D.

*Number of stamens per flower.*—5.
*Anther shape.*—Tubular.
*Anther color.*—Near 12A.
*Pollen color.*—Near 12A.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests has been observed in this cultivar.

Heat and cold resistance: Plants with flowers are hardy to low temperatures about −2° C. Non flowering plants are hardy in the approximate range of 3° C. to −6° C., depending upon duration of cold and amount of moisture in the soil. With adequate water plants are hardy to a high temperature of 49° C.

What is claimed is:

1. A new and distinct cultivar of Chrysanthemum plant named 'Gedi Two Pin' as herein illustrated and described.

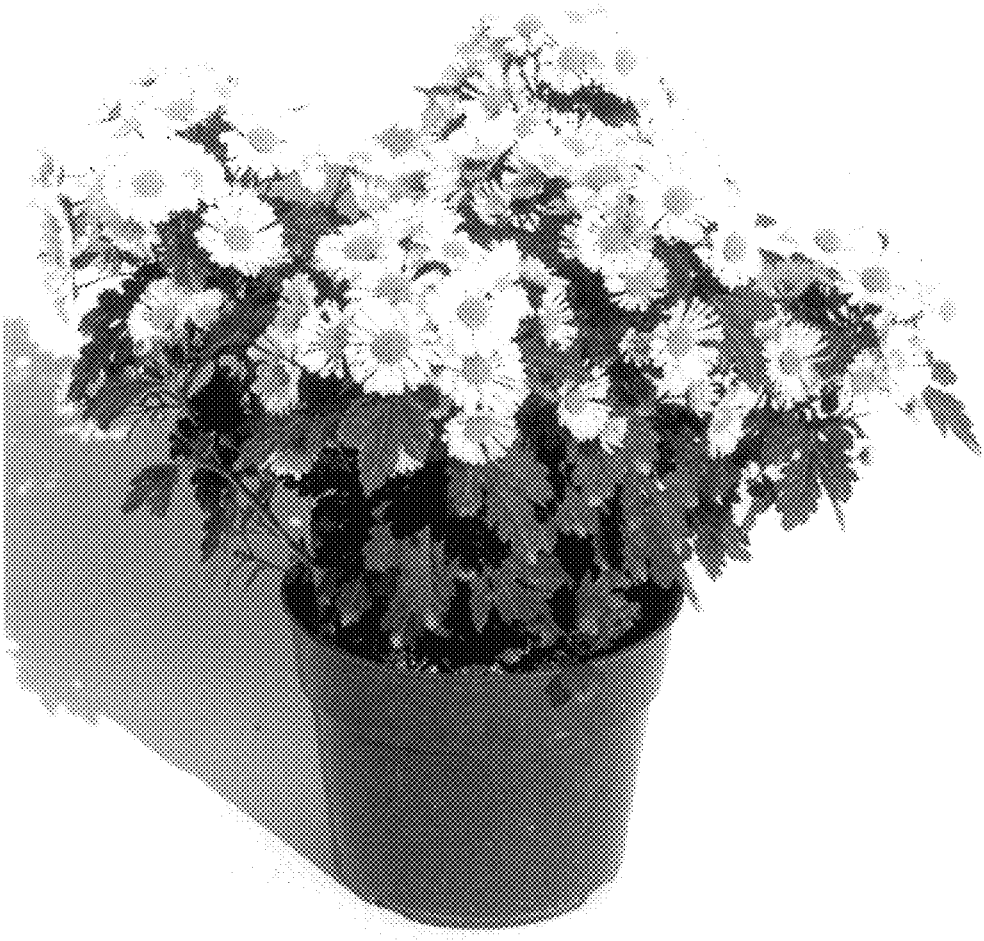

* * * * *